US006797828B1

(12) United States Patent
Shibasaki et al.

(10) Patent No.: US 6,797,828 B1
(45) Date of Patent: Sep. 28, 2004

(54) PROCESSES FOR THE PREPARATION OF 4(5)-AMINO-5(4)-CARBOXAMIDOIMIDAZOLES AND INTERMEDIATES THEREOF

(75) Inventors: Hiroaki Shibasaki, Ibaraki (JP); Fumihiko Nagasaki, Chiba (JP); Mitsuru Takase, Niigata (JP); Satoru Yamazaki, Niigata (JP); Yutaka Ishii, Niigata (JP); Kimihiko Oohata, Niigata (JP)

(73) Assignee: Nippon Soda Co. Ltd., Tokyo (JP)

( * ) Notice: Subject to any disclaimer, the term of this patent is extended or adjusted under 35 U.S.C. 154(b) by 232 days.

(21) Appl. No.: 10/088,425

(22) PCT Filed: Sep. 20, 2000

(86) PCT No.: PCT/JP00/06397

§ 371 (c)(1),
(2), (4) Date: Mar. 15, 2002

(87) PCT Pub. No.: WO01/21592

PCT Pub. Date: Mar. 29, 2001

(30) Foreign Application Priority Data

Sep. 20, 1999 (JP) .......................................... 11-264818
Nov. 19, 1999 (JP) .......................................... 11-330103
Apr. 18, 2000 (JP) ...................................... 2000-116218

(51) Int. Cl.$^7$ .......................................... C07D 233/70
(52) U.S. Cl. .............................. 548/331.1; 548/321.5
(58) Field of Search .................... 548/326.5, 333.5, 548/321.5, 331.1

(56) References Cited

U.S. PATENT DOCUMENTS

| 3,778,446 A | 12/1973 | Weigert |
| 3,806,517 A | 4/1974 | Begland |
| 3,914,279 A | 10/1975 | Begland |

FOREIGN PATENT DOCUMENTS

| EP | 0 898 201 A1 | 2/1999 |
| JP | 59-199705 | 2/1984 |
| JP | 10-168132 | 6/1998 |

OTHER PUBLICATIONS

Booth, et al. The chemistry of nitrilium salts. Part 4. Some reactions of 5-amino-4(C-cyanoformimidoyl)imidazoles obtained from nitrilium trfluoromethanesulphonate salts and diaminomaleonitrile. Chem Soc Perkin Trans 1. 1987;1521–1526.*
B.L. Booth et al., "J.Chem. Soc. Perkin Trans. I:1705, 1990,".
B.L. Booth et al., "J.Chem. Soc. Perkin Trans. I:2120, 1992,".
B.L. Booth et al., "J.Chem. Soc. Perkin Trans., I:669, 1995,".
B.L. Booth et al., "J. Chem. Soc. Perkin Trans. I:1521, 1987,".
R.F. Shuman et al., "J. Org. Chem., 44:4532, 1978,".
B.L. Booth et al., "Journal of Heterocyclic Chemistry; vol. 31 (No. 2) p345–350 (1994),".
B.L. Booth et al, "Tetrahedron Letters; vol. 34 (No. 34) pp. 5503–5506 (1993),".
Booth B L et al., "Synthesis of [1a, 2B. 3a–2–3–bis (benzyloxymethyl)cyclobutyl]imidazol–5–amines: important precursors to cylobut–A derivatives," J. Chem. Soc., Perkins Transactions, 1 ed., p. 669–675, (May 8, 1995).
Alves M J et al., "Synthesis of 5–Amino–4–(cyanoformimidoly)–1H–imidazole: a Reactuve Intermediate for the Synthesis of 6–Carbamoyl–1, 2–dihydropurines and 6–Carbamoypurines," J. Chem Soc., Perkins Trans, 1 ed., p. 1705–1712, (May 8, 1990).
Shuman R F et al., "Chemistry of HCN. 1. Formation and Reactins of N–(Aminomethlidene) diaminomaleonitrile, an HCN Pentamer and Precursor to Adenine," J. Org. Chem., vol. 44 (No. 25), 99. 4532–4536, (May 8, 1979).
Alves M J et al., "Synthesis of 4–and 5–Disubstituted 1–Benzlimidazoles, Important Precursors of Purine Analogs, "Journal of Heterocyclic Chemistry, vol. 31m pp. 345–350, (1993–03).

* cited by examiner

Primary Examiner—Joseph K. McKane
Assistant Examiner—Sonya Wright
(74) Attorney, Agent, or Firm—Dennis G. LaPointe; Mason Law, P.A.

(57) ABSTRACT

The invention provides novel processes for preparing efficiently compounds of general formula (1) (wherein R1 and R2 are each independently hydrogen, optionally substituted C1–C10 alkyl, C3–C14 hydrocarbyl bearing alicyclic skeleton, or the like) and initermediates thereof. Compounds of general formula (I) can be prepared by subjecting compounds of general formula (II) and/or salts thereof to cyclization hydrolysis in an aqueous basic solution. Further, compounds of general formula (II) can be prepared from industrially easily available diaminomaleonitrile in a high yield.

9 Claims, No Drawings

PROCESSES FOR THE PREPARATION OF 4(5)-AMINO-5(4)-CARBOXAMIDOIMIDAZOLES AND INTERMEDIATES THEREOF

This application is a 371 of PCT/JP00/06397.

BACKGROUND OF THE INVENTION

1. Field of the Invention

The present invention relates to processes for simply and efficiently preparing 4(5)-aminoimidazole-5-(4)-carboxamido derivatives and intermediates thereof, which are useful as intermediates of agricultural chemicals and medicines.

2. Description of the Prior Art

Among the compounds represented by formula (I):

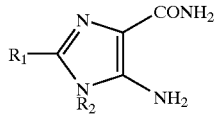

(I)

for example, 1H-4(5)-aminoimidazole-5(4)-carboxamide (wherein $R_1$ and $R_2$ represent hydrogen atoms (hereinafter abbreviated as AICA)), and hydrochloric salts thereof are useful intermediates of medicines, and for example, have been known as basic ingredients of anti-cancer drugs such as dacarbazine and temozoromide, and hepatic protectives such as urazamide.

The processes for synthesizing these include the process wherein 4-nitroimidazole-5-carboxamido is contact-reduced, the process wherein phenylazomalonamidine is reduced and cyclized in formic acid, the process wherein α-amino-α-cyanoacetamido is used as a raw material, and the process wherein a compound having a purine core is decomposed. However, these are insufficient in terms of raw materials, manipulation and industry.

Also, there is the process wherein from industrially available diaminomaleonitrile (hereinafter abbreviated as DAMN), 4,5-dicyanoimidazole is synthesized, which is hydrolyzed (Japanese Patent Publication No. 21026/1966) to synthesize 1H-4(5)-cyanoimidazole-5(4)-carboxamide, which is converted to 1H-4(5)-aminoimidazole-5(4)-carbonitrile (hereinafter abbreviated as AICN) using the Hoffman rearrangement reaction (Japanese Patent Publication No. 10889/1971), and subsequently it is hydrolyzed to synthesize AICA. However, it has been problematic in that a yield from the Hoffman rearrangement reaction is low, steps in the process are many and a yield of the objective is low.

Additionally, B. L. Booth et al. (J. Chem. Soc. Perkin Trans. I:1705, 1990) reported that AICN could be synthesized by cyclizing N-(2-amino-1,2-dicyanovinyl) formamidine (hereinafter abbreviated as AMD) but did not describe the synthesis of AICA.

Also, B. L. Booth et al. (J. Chem. Soc. Perkin Trans., I:2120, 1992; J. Chem. Soc. Perkin Trans., 1:669, 1995) reported that 1-substituted-5-aminoimidazole-4-carbonitrile could be synthesized by cyclizing N-(2-amino-1,2-dicyanovinyl)-N'-substituted-formamidine but did not describe the synthesis of 1-substituted-5-aminoimidazole-4-carboxamide which is one of the target substances of the present invention.

Also, B. L. Booth et al. (J. Chem. Soc. Perkin Trans., I:1521, 1987) reported the process for synthesizing 1,2-substituted imidazole as shown by the following formula.

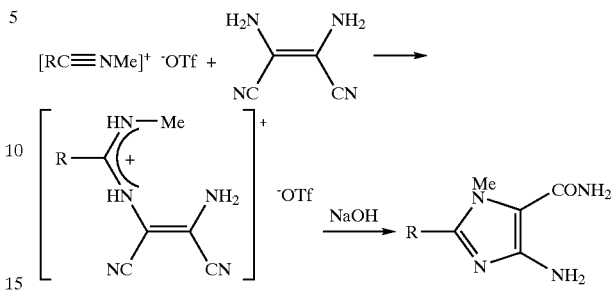

However, it is not suitable for synthesis of N-non-substituents due to the use of a special nitrilium salt, yet it has been problematic in that a yield from cyclization is low and the objective was not obtained with a sufficient yield.

Moreover, it has also been problematic in that in the case of conducting a reaction of alkylation of 1H-4(5)-aminoimidazole-5(4)-carboxamide, both 1- and 3-positions are alkylated and thus its selectivity of position is low.

As the process for synthesis of compounds represented by formula (II) which can be intermediates in synthesis of compounds represented by formula (I), for example, R. F. Shuman et al. (J. Org. Chem., 44:4532, 1979) have reported that N-(2-amino-1,2-dicyanovinyl) formamidine can be synthesized by the method in which DAMN and formamidine acetate are refluxed in ethanol. However, its yield was only 2% and the method is unrealistic as an industrial process for the preparation.

Also, B. L. Booth et al. (J. Chem. Soc. Perkin Trans., I:1705, 1990) have reported that DAMN and triethylorthoformate are reacted in dioxane to synthesize ethyl N-(2-amino-1-,2-@ diaminovinyl) formimidate, which is further reacted with ammonia in chloroform at a low temperature of −20° C. or below using aniline hydrochloride as a catalyst resulting in being capable of synthesizing N-(2-amino-1,2-dicyanovinyl) formamidine. However, in this method there are many problems such as the vexatious complication of reaction manipulation, reaction at a low temperature, many solvents being required, potential environmental pollution by halide solvents and the like, and it was insufficient as an industrial process for the preparation.

SUMMARY OF THE INVENTION

As mentioned above, no simple and efficient process has been known for preparing 4(5)-aminoimidazole-5(4)-carboxamide derivatives and intermediates thereof, which are useful as intermediates of agricultural chemicals and medicines, and the present invention is aimed to provide processes for the preparation thereof.

That is, the present invention relates to;

a process for the preparation characterized in that a compound represented by formula (II):

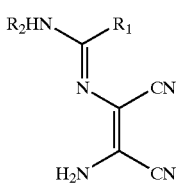

(II)

(wherein $R_1$ and $R_2$ each independently represent a hydrogen atom, an alkyl group of C1 to C10 which may have substituents, a hydrocarbon group of C3 to C14 having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group) and/or a salt thereof are cyclized and hydrolyzed in an aqueous basic solution in a process for preparing a compound represented by formula (I):

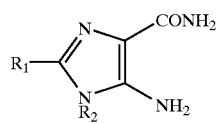

(I)

(wherein $R_1$ and $R_2$ represent the same as defined above) [Constitution 1];

a process for the preparation characterized in that a compound represented by formula (II):

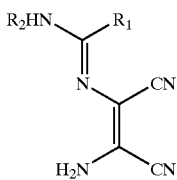

(II)

(wherein $R_1$ represents a hydrogen atom, an alkyl group of C1 to C10 which may have substituents, a hydrocarbon group of C3 to C14 having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group; and $R_2$ represents a hydrogen atom) and/or a salt thereof are cyclized/ hydrolyzed in an aqueous basic solution followed by adjusting the pH to the isoelectric point to precipitate crystal in a process for preparing a compound represented by formula (I):

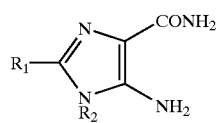

(I)

(wherein $R_1$ and $R_2$ represent the same as defined above) [Constitution 2];

a process for the preparation characterized in that a compound represented by formula (II):

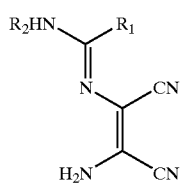

(II)

(wherein $R_1$ represents a hydrogen atom, an alkyl group of C1 to C10 which may have substituents, a hydrocarbon group of C3 to C14 having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group and $R_2$ represents a hydrogen atom) and/or a salt thereof are cyclized/ hydrolyzed in an aqueous basic solution followed by adjusting the pH to 9 to 13 to precipitate crystal in a process for preparing a compound represented by formula (I):

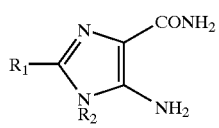

(I)

(wherein $R_1$ and $R_2$ represent the same as defined above). [Constitution 3];

the process for the preparation according to [Constitution 3] characterized in that the pH is adjusted to a range of 11 to 12 [Constitution 4];

the process for the preparation according to any of [Constitution 1] through [Constitution 4] characterized in that a basic compound is sodium hydroxide or potassium hydroxide [Constitution 5];

a process for the preparation characterized in that a compound represented by formula (III):

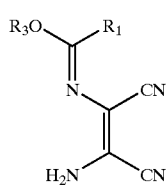

(III)

(wherein $R_1$ represents the same as defined above and $R_3$ represents an alkyl group of C1 to C6) is reacted with ammonia in alcohol of C1 to C5 in a process for preparing a compound represented by formula (II):

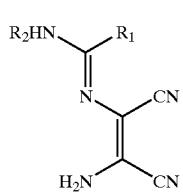

(II)

(wherein $R_1$ represents the same as defined above and $R_2$ represents a hydrogen atom) [Constitution 6];

a process for the preparation characterized in that diaminomaleonitrile is reacted with a compound represented by formula (IV) :R₁C(OR₃) 3 (wherein R₁ and R₃ represent the same as defined above), in alcohol of C1 to C5 to produce a compound represented by general formula (III):

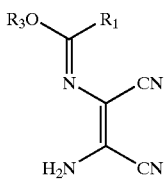

(III)

(wherein R₁ and R₃ represent the same as defined above) followed by being reacted with ammonia in alcohol of C1 to C5 in a process for preparing a compound represented by formula (II):

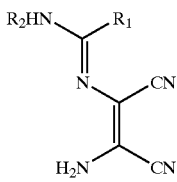

(II)

(wherein R₁ represents the same as defined above and R₂ represents a hydrogen atom) [Constitution 7];

the process for the preparation according to [Constitution 6] or [Constitution 7] characterized in that alcohol of C1 to C5 is methyl alcohol or ethyl alcohol [Constitution 8];

a process for the preparation characterized in that diaminomaleonitrile is reacted with a compound represented by formula (IV):R₁C(OR₃) ₃ (wherein R₁ and R₃ represent the same as defined the above), in alcohol of C1 to C5 in a process for preparing a compound represented by formula (III):

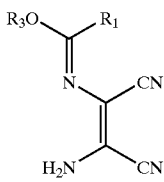

(III)

(wherein R₁ and R₃ represent the same as defined above) [Constitution 9];

the process for the preparation according to [Constitution 9] characterized in that alcohol of C1 to C5 is methyl alcohol or ethyl alcohol [Constitution 10];

a process for the preparation characterized in that a compound of the formula (V): R₁CN (wherein R₁ represents the same as defined above) is reacted with diaminomaleonitrile in the presence of an acid in a process for preparing a compound represented by formula (II):

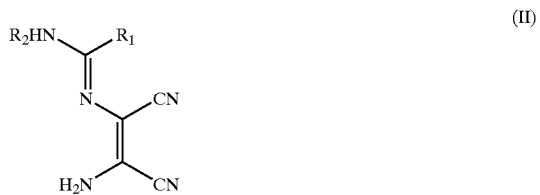

(II)

(wherein R₁ represents an alkyl group of C1 to C10 which may have substituents, a hydrocarbon group of C3 to C14 having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group and R₂ represents a hydrogen atom) and a salt thereof [Constitution 11];

the process for the preparation according to [Constitution 11] characterized in that an acid is anhydrous hydrochloric acid [Constitution 12];

a compound represented by formula (II):

(II)

(wherein R₁ represents the same as defined above and R₂ represents a hydrogen atom), and salts thereof [Constitution 13];

a process for the preparation characterized in that diaminomaleonitrile and a compound represented by formula (VI): R₁CONHR₂ (wherein R₁ and R₂ each independently represent a hydrogen atom, an alkyl group of C1 to C10 which may have substituents, a hydrocarbon group of C3 to C14 having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group) are reacted with a compound selected from the group consisting of phosphorous oxychloride, phosphorous trichloride, phosphorous pentachloride, phosphorous oxybromide, diphosphoryl chloride, sulfonyl chloride, sulfuryl chloride, phosgene, diphosgene, triphosgene, and chloroformate trichloromethyl ester in a process for preparing a compound represented by formula (II):

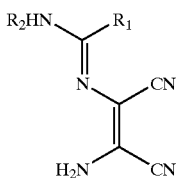

(II)

wherein (R₁ and R₂ represent the same as defined above) [Constitution 14];

the process for the preparation or the compound according to any of [Constitution 1] through [Constitution 3], [Constitution 6], [Constitution 7], [Constitution 9], [Constitution 11], [Constitution 13] or [Constitution 14] wherein $R_1$ in formulae (I) through (VI) is a hydrogen atom, an unsubstituted alkyl group of C1 to C10 having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups, a hydrocarbon group of C3 to C14 having alicyclic skeletons, an unsubstituted alkenyl group of C1 to C10 having straight or branched chains, an alkenyl group of C1 to C10 having straight or branched chains substituted with halogen atoms, hydroxyl, alkoxy, phenyl, substituted phenyl groups, an unsubstituted alkynyl group of C1 to C10 having straight or branched chains, an alkynyl group having straight or branched chains substituted with halogen atoms, hydroxyl, alkoxy, phenyl, substituted phenyl groups, a phenyl group, a phenyl group substituted with halogen atoms, alkyl, alkoxy, phenyl, substituted phenyl, heterocyclic, aralkyl, heterocyclic alkyl groups, an unsubstituted aralkyl group having straight or branched chains, an aralkyl group having straight or branched chains substituted with halogen atoms, alkyl, alkoxy, phenyl, substituted phenyl, heterocyclic, aralkyl, heterocyclic alkyl groups, an unsubstituted heterocyclic group, a heterocyclic group substituted with halogen atoms, alkyl, alkoxy, phenyl, substituted phenyl, heterocyclic, aralkyl, heterocyclic alkyl groups, an unsubstituted heterocyclic alkyl group having straight or branched chains, a heterocyclic alkyl group having straight or branched chains substituted with halogen atoms, alkyl, alkoxy, phenyl, substituted phenyl, heterocyclic, aralkyl, heterocyclic alkyl groups, an N-unsubstituted or substituted carbamoyl group, or an alkoxycarbonyl group [Constitution 15];

the process for the preparation according to [Constitution 1] or [Constitution 14] wherein R₂ in formulae (I), (II) and (VI) is an unsubstituted alkyl group of C1 to C10 having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups, a hydrocarbon group of C3 to C14 having alicyclic skeletons, an unsubstituted alkenyl group of C1 to C₁₀ having straight or branched chains, an alkenyl group of C1 to C10 having straight or branched chains substituted with halogen atoms, hydroxyl, alkoxy, phenyl, substituted phenyl groups, an unsubstituted alkynyl group of C1 to C10 having straight or branched chains, an alkynyl group having straight or branched chains substituted with halogen atoms, hydroxyl, alkoxy, phenyl, substituted phenyl groups, a phenyl group a phenyl group substituted with halogen atoms, alkyl, alkoxy, phenyl, substituted phenyl, heterocyclic, aralkyl, heterocyclic alkyl groups, an unsubstituted aralkyl group having straight or branched chains, an aralkyl group having straight or branched chains substituted with halogen atoms, alkyl, alkoxy, phenyl, substituted phenyl, heterocyclic, aralkyl, heterocyclic alkyl groups, an unsubstituted heterocyclic group, a heterocyclic group substituted with halogen atoms, alkyl, alkoxy, phenyl, substituted phenyl, heterocyclic, aralkyl, heterocyclic alkyl groups, an unsubstituted heterocyclic alkyl group having straight or branched chains, a heterocyclic alkyl group having straight or branched chains substituted with halogen atoms, alkyl, alkoxy, phenyl, substituted phenyl; heterocyclic, aralkyl, heterocyclic alkyl groups, an N-unsubstituted or substituted carbamoyl group, or an alkoxycarbonyl group [Constitution 16];

the process for the preparation according to any of [Constitution 1] through [Constitution 3], [Constitution 6], [Constitution 7], [Constitution 9], [Constitution 11], or [Constitution 14] wherein R₁ in formulae (I) through (VI) is a hydrogen atom, an unsubstituted alkyl group of C1 to C10 having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups [Constitution 17];

the process for the preparation according to any of [Constitution 1] through [Constitution 3], [Constitution 6], [Constitution 7], [Constitution 9], [Constitution 11], or [Constitution 14] wherein R₁ in general formulae (I) through (VI) is an unsubstituted alkyl group of C1 to C10 having straight or branched chains [Constitution 18];

the compound according to [Constitution 13] wherein R₁ in formula (II) is an unsubstituted alkyl group of C1 to C10 having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups, a hydrocarbon group of C3 to C14 having alicyclic skeletons, an unsubstituted alkenyl group of C1 to C10 having straight or branched chains, an alkenyl group of C1 to C10 having straight or branched chains substituted with halogen atoms, hydroxyl, alkoxy, phenyl, substituted phenyl groups, an unsubstituted alkynyl group of C1 to C10 having straight or branched chains, an alkynyl group having straight or branched chains substituted with halogen atoms, hydroxyl, alkoxy, phenyl, substituted phenyl groups, a phenyl group, a phenyl group substituted with halogen atoms, alkyl, alkoxy, phenyl, substituted phenyl, heterocyclic, aralkyl, heterocyclic alkyl groups, an unsubstituted aralkyl group having straight or branched chains, an aralkyl group having straight or branched chains substituted with halogen atoms, alkyl, alkoxy, phenyl, substituted phenyl, heterocyclic, aralkyl, heterocyclic alkyl groups, an unsubstituted heterocyclic group, a heterocyclic group substituted with halogen atoms, alkyl, alkoxy, phenyl, substituted phenyl, heterocyclic, aralkyl, heterocyclic alkyl groups, an unsubstituted heterocyclic alkyl group having straight or branched chains, a heterocyclic alkyl group having straight or branched chains substituted with halogen atoms, alkyl, alkoxy, phenyl, substituted phenyl, heterocyclic, aralkyl, heterocyclic alkyl groups, an N-unsubstituted or substituted carbamoyl group, or an alkoxycarbonyl group [Constitution 19];

the compound according to [Constitution 13] wherein $R_1$ in formula (II) is an unsubstituted alkyl group of C1 to C10 having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups [Constitution 20]; and the compound according to [Constitution 13] wherein $R_1$ in formula (II) is an unsubstituted alkyl group of C1 to C10 having straight or branched chains[Constitution 21].

The present invention relates to a process for preparing 4-aminoimidazole-5-carboxamide derivatives represented by formula (I). In formula (I), $R_1$ and $R_2$ each independently represent a hydrogen atom, an alkyl group of C1 to C10 which may have substituents, a hydrocarbon group of C3 to C14 having alicyclic skeletons, an alkynyl group which may have substituents, an aryl group which may have substituents, an aralkyl group which may have substituents, a heterocyclic group which may have substituents, or a heterocyclic alkyl group which may have substituents.

Specific examples of alkyl groups of C1 to C10 which may have substituents can exemplify methyl, ethyl, n-propyl, iso-propyl, n-butyl, t-butyl, n-decyl, methoxymethyl, methylthiomethyl, 4-acetoxyl3-acetoxymethyl1-butyl, 4-hydroxyl3-hydroxymethyl1-butyl, 2-hydoroxyethoxymethyl, 2-hydroxyl1-hydroxymethyl1-ethoxymethyl, 4-hydroxyl2-hydroxymethyl1-butyl, 5-(N-methyl carbamoyloxy) butyl, hydroxycarbonylmethyl, 2-chloroethyl, 2-dimethylaminoethyl, N-substituted-2-asparagyl groups and the like. Specific examples of hydrocarbon groups of C3 to C14 having alicyclic skeletons can exemplify cyclopropyl, cyclopropylmethyl, cyclohexyl, cyclohexylmethyl, 1-adamantil, 1-adamantilmethyl, bicyclo [2,2,1] hepta-2,3-epoxyl5-yl, cyclobutyl, 2,3-hydroxymethylcyclobutyl, cyclopenyl, 1,2-hydroxymethylcyclopropylmethyl groups, and the like. Specific examples of alkenyl groups which may have substituents can exemplify vinyl, 2-methylvinyl, 1,2-dichlorovinyl, cinnamoyl, 3',4'-dimethoxycinnamoyl, allyl, 1-methylally, 3-chloro-2-propenyl, 3-hydroxyl1-butenyl, 3-methoxyl2-propenyl groups and the like. Specific examples of alkynyl groups which may have substituents can exemplify ethynyl, 2-propynyl, 2-chloroethynyl, 3-chloro-2-propynyl, 3-hydroxyl1-butenyl, 3-alkoxyl1-butenyl, 3-pheny1-2-propynyl, 3-(3,4-dimethoxyphenyl)-2-propenyl groups and the like. Specific examples of aryl groups which may have substituents can exemplify phenyl, 4-methylphenyl, 4-chlorophenyl, 2,3-dimethylphenyl, 3,5-dimethylphenyl, 2,6-dimethylphenyl, 4-methoxyphenyl, 3-phenoxyphenyl, 4-phenylphenyl, 4-(2-chlorophenyl) phenyl, 4-(3-isoxazolylphenyl)phenyl, 3-benzylphenyl, 2-pyridylmethylphenyl groups andthe like. Specific examples of aralkyl groups which may have substituents can exemplify benzyl, 1-methylbenzyl, phenethyl, 4-methylphenylmethyl, 4-chlorophenylmethyl, 3-methoxyphenylmethyl, 3-phenoxyphenylmethyl, 4-pheny1-phenylmethyl, 4-(2-3-tetrazolyl) phenyl) phenylmethyl, 4-(2-pyridyl) phenylmethyl, 3-9 benzylphenylmethyl, 3-(2-pyridylmethyl) phenylmethyl, 4-phenyl-1-methylmethyl groups and the like. Specific examples of heterocyclic groups which may have substituents can exemplify 2-pyridyl, 6-methyl-2-pyridyl, 6-chloro-2-pyridyl, 6-methoxyl2-pyridyl, 4-phenyl-2-pyridyl, 4-(4-methylphenyl)-2-pyridyl, 6-(2-pyridyl)-2-pyridyl, 6-(2-pyridylmethyl)-2-pyridyl, 4-tetrahydropyranyl, 3-isoxazolyl, β-D-arabinofuranosyl, β-D-ribofuranosyl, 5-benzylamino-5-deoxylβ-D-ribofuranosyl, 5-O-methylβ-D-ribofuranosyl, 5-phosphonyl-5-deoxylβ-D-ribofuranosyl, 2-deoxylβ-D-arabinofuranosyl, 2-deoxylβ-D-ribofuranosyl groups and the like. Specific examples of heterocyclic alkyl groups which may have substituents can exemplify 2-pyridylmethyl, 3-pyridylmethyl, 6-chloro-pyridylmethyl, 6-methoxyl2-pyridylmethyl, 3-phenyl-2-pyridylmethyl, 4-(4-methylphenyl)-2-pyridylmethyl, 6-(2-pyridyl)-2-pyridylmethyl, 4-benzyl -2-pyridylmethyl, 4-(3-isoxazoryl)-2-pyridylmethyl, 1-methyl1-5-chloro-4-pyrazolylmethyl groups and the like. Specific examples of N-unsubstituted or substituted carbamoyl groups can exemplify N-methylcarbamoyl, N-phenylcarbamoyl groups and the like. Specific examples of alkoxycarbonyl groups can exemplify t-butoxycarbonyl, methoxycarbonyl groups and the like.

In the compounds represented by formula (II) used in the present invention, $R_1$ and $R_2$ represent the same as defined above, and can exemplify the same specific examples.

The cyclization and hydrolysis reaction of the compound represented by formula (II) can exemplify , for example, the process wherein 0.5 to 10 L of water per 1 mole of the compound represented by formula (II) is added followed by conducting the reaction for 1 to 48 hours using 1 to 10 equivalents, preferably 2 to 8 equivalents of a basic compound. The compound represented by formula (II) can also be added to the reaction system in the form of salt such as hydrochloride or as a mixture with a salt. But, when using the compound represented by formula (II) in the form of salt, the quantity of the basic compound used in the reaction does not include a quantity used to neutralize the salt.

The reaction temperature is also related to the reaction time period, and the reaction is usually carried out at normal room temperature to refluxing temperature. In this case, when a low concentration of a base is used, a reaction time period is shortened and a low reaction temperature is chosen, the reaction is not sometimes completed sufficiently. After completion of the reaction, the compound represented by formula (I) can be obtained by cooling the aqueous solution to room temperature followed by extracting with the solvent, or by neutralizing the reaction solution followed by distilling out water and extracting with the solvent.

As required, the obtained compound represented by formula (I) can be dissolved in a nonaqueous solvent, or an acid such as hydrogen chloride gas or concentrated hydrochloric acid can be added to the reaction solution to precipitate the salt, and then the salt can be isolated by filtration. The generated salt is primarily defined depending on the acid used, however, after neutralizing the salt, another acid can be added or direct salt exchange can be performed to synthesize various types of salts. The compound represented by formula (I) can also be obtained by neutralizing a salt yielded as crystal.

When $R_2$ is a hydrogen atom in the compounds represented by formulae (I) and (II), after completion of the reaction, the aqueous solution can be cooled to room temperature, the pH is adjusted to the isoelectric point, and then the generated crystal can be filtrated to yield the target imidazole compound represented by formula (I) with a sufficient purity. The isoelectric point is varied depending on the compounds, and adjusting the pH to 9 to 13, preferably 11 to 12 affords a good result.

After completion of the reaction and prior to cooling to room temperature and adjusting the pH, setting a tail end process using activated carbon can sometimes improve the purity of obtained crystal or resolve coloring issues in some cases.

Aqueous basic solutions used herein are not especially limited so long as it is an aqueous solution of a compound exhibiting to be basic, and can specifically exemplify aqueous solutions of alkali metallic or alkali earth metallic hydroxides such as sodium hydroxide, potassium hydroxide, magnesium hydroxide, calcium hydroxide, aluminium hydroxide and the like, and carbonates such as sodium carbonate, sodium hydrogen carbonate, potassium carbonate, potassium hydrogen carbonate, magnesium carbonate, and the like. Especially, an aqueous solution of sodium hydroxide or potassium hydroxide is preferable.

In the compounds represented by formula (III), $R_1$ represents the same as defined above and can exemplify the same specific examples. $R_3$ represents an alkyl group of C1 to C6, and can specifically exemplify methyl, ethyl, n-propyl, isopropyl, n-butyl, s-butyl, n-penyl, n-hexyl groups and the like.

The processes for preparing the compound represented by formula (II) wherein $R_2$ is a hydrogen atom from the compound represented by formula (III) and ammonia can exemplify (1) a process wherein ammonia gas is injected into a C1 to C5 alcohol solution or suspension of the compound represented by formula (III), (2) a process wherein ammonia gas is injected into and dissolved in C1 to C5 alcohol followed by directly adding the compound represented by formula (III) or by adding a C1 to C5 alcohol solution or suspension of the compound represented by formula (III), (3) a process wherein a C1 to C5 alcohol solution or suspension of the compound represented by formula (III)is added to ammonia condensed at a low temperature, and (4) a process wherein an aqueous solution of ammonia instead of ammonia gas is used in the above (1) or (2), and the like.

Examples of C1 to C5 alcohol can specifically exemplify methanol, ethanol, n-propatol, isopropanol, n-butanol, isobutanol, t-butanol and the like. In particular, methanol and ethanol are preferable in light of solubility of raw materials and products, easiness in recovery and distillation, cost and the like.

The reaction progresses either under cooling or at the solvent refluxing temperature. However, in light of solubility of ammonia and exothermic heat at dissolution, starting the reaction under cooling is preferable, and specifically reacting at −20° C. to 20° C., preferably 0 to 100° C. is preferred. The reaction time periods are not particularly limited but a range of 0.5 to 10 hours is best exemplified.

After termination of the reaction, isolation of the compound represented by formula (II) can be carried out, for example, by filtration. In order to reduce a portion dissolved in the solvent and improve a yield, it is preferable to precipitate sufficiently by cooling.

Such processes can yield the compound represented by formula (II) with a high purity. However, when more highly purified products are required, purification can be carried out by recrystallization.

The compound represented by formula (III) can be prepared from DAMN and trialkylorthoformate represented by formula (IV). In the compounds represented by formula (IV), $R_1$ and $R_3$ represent the same as defined above and can exemplify the same specific examples.

The process for preparing the compound represented by formula (III) can be carried out in an alcohol solvent either at room temperature or on heating. Alcohol solvents can exemplify, for example, methanol, ethanol, n-propanol, isopropanol, n-butanol, isobutanol, t-butanol and the like. In particular, methanol and ethanol are preferable in the light of solubility of raw materials and products, easiness in recovery and distillation, cost and the like.

Furthermore, since alcohol of a lower alkyl derived from a raw material used in the reaction is produced secondarily, it is preferable that an alcohol solvent to be used is to be the same type as the secondarily produced alcohol of the lower alkyl in terms of separation and recovery. Additionally, it is preferable that the type of alcohol solvent to be used is the same as the solvent in the following step at which the compound is reacted with ammonia in terms of recovering and utilizing the solvent.

The reaction temperatures are not especially limited. However, the reaction is slow and a long time is required at a lower temperature, whereas it is necessary to note lowering in purity due to an increase in by-products (mainly 4,5-dicyanoimidazole, a cyclized product) while the raw materials extinguish in a short time at a higher temperature. The range of room temperature to solvent refluxing temperatures is preferable as the reaction temperature. The reaction time period are not particularly limited but a range of 0.5 to 10 hours is best exemplified.

After termination of the reaction, isolation of the compound represented by formula (III) can be carried out, for example by filtration. In such a case, in order to reduce a portion dissolved in the solvent and improve a yield, it is preferable to precipitate significantly by cooling to 0° C. to room temperature. Such processes can yield the compound represented by formula (III) with a high purity. However, when more highly purified products are required, purification can be carried out by recrystallization.

A process for preparing the compound represented by formula (II) wherein $R_2$ is a hydrogen atom can exemplify a process wherein the compound of the formula (V) $R_1CN$ is reacted with diaminomaleonitrile in the presence of an acid.

In the compound of the formula(V) $R_1CN$, $R_1$ represents the same as defined above except that it does not include a hydrogen atom, and can exemplify the same specific examples. Acids used herein are not especially limited so long as it is a compound exhibiting to be acidic, and can specifically exemplify sulfuric acid, hydrobromic acid, hydriodic acid, nitric acid, p-toluene sulfonic acid, methane sulfonic acid, trifluoromethane sulfonic acid and the like. Hydrochloric acid is preferable and anhydrous hydrochloric acid is more preferable in terms of reaction manipulation and cost.

Standard solvents usable within industry except alcohols and ketones can be used as solvents used in the manufacture according to the above processes for preparing the compound represented by formula (II). Specifically, hydrocarbon solvents such as benzene, toluene, xylene, cyclohexane and the like, halide solvents such as chloroform, methylene chloride, chlorobenzene, dichlorobenzene and the like, ether solvents such as diethyl ether, dioxane, tetrahydrofuran, diethyleneglycol dimethylether, and the like can be exemplified, and can be used alone or in mixture of two or more. When the nitrites represented by general formula (V) and used in the reaction is a liquid at the reaction temperature, it is preferable that it is used at an excess quantity and as such is used as the solvent.

A quantity of the nitrile compound represented by formula (V) is not specifically limited so long as it is an equivalent or more based on a quantity of DAMN used. When it is used as the solvent, an excess quantity is used. The reaction of a nitrile compound with DAMN is usually carried out within a range of −80° C. to 40° C. It is especially preferable to carry out within a range of −20° C. to 30° C. A quantity of the acid used is necessary to be one equivalent or more based on a quantity of the DAMN usually used. Preferably 2.0 equivalents or more, and more preferably a range of 2 to 5 equivalents are appropriate.

For the reaction either a process wherein the acid is added to the nitrile compound followed by adding DAMN, a process wherein the acid is added to the mixture of the nitrile compound and DAMN, or a process wherein the nitrile compound is added to the mixture of DAMN and the acid can be employed. For example, when hydrogen chloride gas is used as an anhydrous hydrochloric acid, a process can be exemplified wherein using the nitrile compound as the solvent, hydrogen chloride gas is injected at 0° C. or below followed by adding DAMN at the same temperature. In this case, the reaction can also be carried out by injecting hydrogen chloride gas into the mixture of the nitrile compound and DAMN at 0° C. or below.

In many cases, the reaction product is precipitated in the system as a salt with the acid used, and only filtration is needed to yield the compound having a purity capable of being tested in the next reaction. If the crystal is not precipitated, crystallization can be carried out by concentrating the solvent followed by injecting into the non-polar solvent such as hexane and the like or by adding the non-polar solvent.

The product is provided for the next reaction either as an aqueous solution isolated from the solvent by adding water after the reaction to make the salt migrate into the aqueous layer, or as an acid-free amidine compound by adding an equivalent or more of the basic compound based on the acid used to neutralize followed by being extracted with the solvent. The acid-free amidine compound can also be obtained by neutralizing the salt obtained as crystal.

The amidine compounds represented by formula (II) wherein $R_2$ is a hydrogen atom and salts thereof are novel compounds and useful compounds as intermediates in synthesis of the imidazole compounds represented by formula (I) and the like. The generated salt of amidine is primarily defined depending on the acid used, however, after neutralizing the salt, another acid can be added or a direct salt exchange can be performed to produce various types of salts.

As a process for preparing the compound represented by general formula (II), a process can be exemplified wherein diaminomaleonitrile and the compound represented by formula (VI) $R_1CONHR_2$ are reacted with the compound (hereinafter abbreviated as phosphorous oxychloride etc.) selected from the group consisting of phosphorous oxychloride, phosphorous trichloride, phosphorous pentachloride, phosphorous oxybromide, diphosphoryl chloride, sulfonyl chloride, sulfurylchloride, phosgene, diphosgene, triphosgene, and chloroformate trichloromethyl ester.

In the compounds represented by formula (VI), $R_1$ and $R_2$ represent the same as defined for $R_1$ and $R_2$ in formula (I) in [Constitution 1], and can exemplify the same specific examples.

Standard solvents usable within industry except alcohols and ketones can be used as solvents used in the manufacture according to the above processes for preparing the compound represented by formula (II). Specifically, hydrocarbon solvents such as benzene, toluene, xylene, cyclohexane and the like, halide solvents such as chloroform, methylene chloride, chlorobenzene, dichlorobenzene and the like, ether solvents such as diethylether, dioxane, tetrahydrofuran, diethyleneglycol dimethylether, and the like can be exemplified, and can be used alone or in mixture of two or more to synthesize.

The above reaction can employ either (1) a process wherein phosphorous oxychloride etc., is added to a solution or suspension of DAMN and the compound represented by formula (VI), (2) a process wherein phosphorous oxychloride etc., is added to a solution or suspension of the compound represented by formula (VI) followed by adding DAMN, or (3) a process wherein a solution or suspension of DAMN and the compound represented by formula (VI) is added to a solution or suspension of phosphorous oxychloride etc. Especially, the process of (1) is preferred.

The reaction temperature is not especially limited, but the reaction is preferably carried out at a lower temperature in terms of control of the reaction. Specifically, the reaction is preferably carried out at −20° C. to 40° C., more preferably at −10° C. to 40° C., and still more preferably at 0° C. to 30° C. In particular, when phosphorous oxychloride etc., is added or when being added to phosphorous oxychloride etc., the reaction is preferably carried out at a still lower temperature, specifically at −20° C. to 30° C., and more preferably at −10° C. to 10° C.

A quantity of the compound represented by formula (VI) to be used is in a range of 1.0 to 2.0 equivalents based on a quantity of DAMN. A range of 1.0 to 1.2 equivalents is preferable. A quantity of phosphorous oxychloride etc., to be used is in a range of 1.0 to 1.5 equivalents based on a quantity of the compound represented by formula (VI). The range of 1.0 to 1.1 equivalents is preferable.

A quantity of the solvent to be used is not especially limited, but a range of 0.1 to 10 L, more preferably 0.3 to 2 L, and still more preferably 0.3 to 0.6 L based on one mole of DAMN are preferable.

The compound represented by formula (II) can be obtained by neutralizing the reaction solution using a basic compound after completion of the reaction followed by filtrating precipitated crystal or by being extracted with the solvent. Examples of basic compounds used in this case can specifically exemplify alkali metallic or alkali earth metallic hydroxides such as sodium hydroxide, potassium hydroxide, magnesium hydroxide and the like, alkali metallic or alkali earth metallic carbonates such as sodium carbonate, sodium hydrogen carbonate, potassium carbonate, calcium carbonate, and the like.

BEST MODE FOR CARRYING OUT THE INVENTION

The present invention is described in detail using the examples, but the present invention is not limited to the examples.

EXAMPLES

Example 1

Water (50 ml) and an aqueous solution of 25% NaOH (43.0 g) were added to 8 g of N-(2-amino-1,2-dicyanovinyl) formamidine (hereinafter abbreviated as AMD), and reacted under reflux for 2 hours. This aqueous solution was cooled to room temperature or below and adjusted the pH to 7 by adding 35% hydrochloric acid. The reaction solution was concentrated and exsiccated under reduced pressure followed by adding ethanol, and subsequently insoluble sodium chloride was filtrated and removed. The filtrate was treated with activated carbon and then concentrated to afford an ethanol solution of AICA. To lower the pH to 3 or less, 35% hydrochloric acid was added to this, cooled to 10° C. or less, and subsequently generated crystal was filtrated. This crystal was dried to yield 8.1 g of 4(5)-aminoimidazole-5-carboxamide (hereinafter abbreviated as AICA) hydrochloride (yield: 84%).

Melting point: 250–252° C. (decomposition)

Example 2

After 75 ml of isobutyronitrile was cooled to 0° C., 9.3 g of hydrogen chloride gas was injected at a range of 0° C. to 50° C. followed by adding 11.0 g of DAMN. The solution was reacted at 20° C. to 25° C. for 20 hours, and the reaction solution was cooled to 5° C. or below followed by filtrating the resultant crystal. The crystal was washed twice with 15 ml of isobutyronitrile, and subsequently dried to yield 21.4 g of N-(2-amino 1,2-9 dicyanovinyl) isobutylamidine hydrochloride. 1H NMR (CDCl$_3$, TMS standard) δ 1.24 (d, 6H, CH3), 2.91(m, 1H, CH), 8.29(s, 2H, NH2), 9.25, 9.86, 10.95(3H, amidine HCl).

Decomposition point: 137–139° C.

Water (20 ml) and 13.2 g of 25% NaOH aqueous solution were added to 4.3 g of the resultant N-(2-amino 1,2-dicyanovinyl) isobutylamidine hydrochloride, and reacted under reflux for 2 hours. This aqueous solution is cooled to room temperature or below and the pH is adjusted to a range of 11 to 12. The reaction solution was cooled to 5° C. or below, and the resultant crystal was filtrated. This crystal was dried to yield 2.4 g of 1H-5(4)-amino-2-isopropylimidazole-4(5)-carboxamide (yield: 70%). 1H NMR (CDCl$_3$, TMS standard) δ 1.19(d, 6H, CH3), 2.80(m, 1H, CH), 5.53(s, 2H, NH2), 6.62(s, 2H, CONH2), 11.15(1H, imidazole, NH).

Melting point: 218–224° C.

Example 3

N-butyronitrile (78 ml) was cooled to 10° C., and 7.15 g of hydrogen chloride gas was injected followed by adding 10.8 g of DAMN. The solution was reacted at 20° C. to 25° C. for 48 hours, and the reaction solution was cooled to 5° C. or below followed by filtrating the resultant crystal. The crystal was washed twice with 10 ml of n-butyronitrile, and subsequently dried to yield 26.7 g of N-(2-amino-1,2-dicyanovinyl) butylamidine hydrochloride. 1H NMR (CDCl$_3$, TMS standard) δ 0.95(t, 3H, CH3), 1.70(m, 2H, CH2), 2.50(m, 2H, CH2), 8.33(s, 2H, NH2), 9.19, 10.06, 11.01(3H, amidine HCl).

Decomposition point: 148–151° C.

Water (50 ml) and 54 g of 25% NaOH aqueous solution were added to 9.28 g of the resultant N-(2-amino-1,2-dicyanovinyl) butylamidine hydrochloride, and reacted under reflux for 14 hours. This aqueous solution was cooled to room temperature or below and the pH was adjusted to a range of 11 to 12 to generate crystal. The reaction solution was cooled to 5° C. or below, and the resultant crystal was filtrated and dried to yield 4.1 g of 1H-5(4)-amino-2-propylimidazole-4(5)-carboxamide (yield: 62.3%). 1H NMR (CDCl$_3$, TMS standard) δ 1.19(d, 6H, CH3), 2.80(m, 1H, CH), 5.53(s, 2H, NH2), 6.62(s, 2H, CONH2), 11.15(1H, imidazole, NH).

Melting point: 199–201° C.

Example 4

DAMN (30.0 g) and 32.4 g of trimethylorthoformate were added to 60 ml of methanol, and stirred with heating at 65° C. for 2 hours under a nitrogen atmosphere. The reaction solution was cooled to 5° C. or below, and precipitated crystal was filtrated and washed with 20 ml of methanol. The crystal was dried under vacuum to yield 33.6 g of methyl N-(2-amino-1,2-dicyanovinyl) formimidate (yield: 80.6%, purity: 95.1). The solvent of the filtrate together with the washings was distilled off to afford 2.4 g of the secondary crystal of methyl N-(2-amino-1,2-dicyanovinyl) formimidate (purity: 26.5%).

Example 5

DAMN (200.0 g) and 301.6 g of triethylorthoformate were added to 410 ml of ethanol, and stirred with heating at 65° C. for 2 hours under a nitrogen atmosphere. The reaction solution was cooled to 3° C., and precipitated crystal was filtrated. After washing with 60 ml of ethanol, the crystal was dried under vacuum to yield ethyl N-(2-amino-1,2-dicyanovinyl) formimidate (yield: 88.6%, purity: 98.0%).

The solvent of the filtrate together with the washings was distilled off to afford 28.5 g of the secondary crystal of ethyl N-(2-amino-1,2-dicyanovinyl) formimidate (purity: 44.6%)

Example 6

Ethyl N-(2-amino-1,2-dicyanovinyl)formimidate (40.0 g) was added to 245 ml of ethanol, cooled with stirring to 5° C., and 23 g of ammonia was injected over 2 hours followed by stirring as such for 7 hours. Excess ammonia was degassed at room temperature under reduced pressure followed by cooling to 5° C. The precipitated crystal was filtrated, washed with 20 ml of ethanol and dried under vacuum to afford 28.1 g of AMD (yield: 85.4%, purity: 96.9%). The solvent of the filtrate together with the washings was distilled off to afford 4.4 g of the secondary crystal of AMD (purity: 72.3%).

Example 7

DAMN (0.1 mole, 11.03 g, purity: 98%) and 4.95 g of formamide (0.11 mole) were dissolved in 100 ml of THF and cooled to 5° C. Maintaining the inner temperature at 5° C. 16.87 g of phosphorous oxychloride (0.11 mole) was added dropwise over 30 min, and then stirred overnight with gradually elevating the solution temperature to room temperature. The reaction solution was neutralized with 383.92 g of 5% sodium hydrogen carbonate aqueous solution. The precipitated crystal was filtrated and dried to afford 9.20 g of AMD (yield: 68.1%).

Example 8

DAMN (11.03 g, 0.1 mole, purity: 98%) and 4.95 g of formamide (0.11 mole) were added to 50 ml of THF and cooled to 5° C. Maintaining the inner temperature at 5° C., 16.87 g of phosphorous oxychloride (0.11 mole) was added dropwise over 45 min, and then stirred overnight and gradually elevating the solution temperature to room temperature. The reaction solution was neutralized with 505.33 g of 5% sodium hydrogen carbonate aqueous solution. The precipitated crystal was filtrated and dried to afford 12.39 g of AMD (yield: 91.7%).

Example 9

DAMN (110.32 g, 1.0 mole, purity: 98%) and 49.54 g of formamide (1.1 mole) were dissolved in 500 ml of THF and cooled to 5° C. Maintaining the inner temperature at 5° C., 168.66 g of phosphorous oxychloride (1.1 mole) was added dropwise over 1.5 hours, and then stirred for 4 hours and gradually elevating the solution temperature to room temperature. The reaction solution was neutralized with 5362.9 g of 5% sodium hydrogen carbonate aqueous solution. The precipitated crystal was filtrated and dried to afford 118.17 g of AMD (yield: 87.4%).

(f) Industrial Applicability

As mentioned above, the process of the present invention is suitable as an industrial method for production because it can use industrially easily available diaminomaleonitrile as a raw material and yet short steps and a simple tail end process can produce the target 4(5)-aminoimidazole-5(4)-carboxamide derivatives in a good yield and purity. The resultant 4(5)-aminoimidazole-5(4)-carboxamide derivatives are compounds widely used as intermediates of agricultural chemicals and medicines. N-(2-amino-1,2-dicyanovinyl) amidine which is an intermediate in production of 4(5)-aminoimidazole-5(4)-carboxamide derivatives becomes possible to be obtained from diaminomaleonitrile by simpler methods compared to the conventional methods, and this is a useful compound as an intermediate of other heterocyclic syntheses.

What is claimed is:

1. A process for the preparation characterized in that a compound represented by formula (II):

(II)

wherein $R_1$ and $R_2$ each independently represent a hydrogen atom, an alkyl group of $C_1$ to $C_{10}$ which may have substituents, a hydrocarbon group of $C_3$ to $C_{14}$ having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group and/or an inorganic salt thereof are cyclized and hydrolyzed in an aqueous basic solution involving 1–10 moles of a basic compound per 1 mole of the compound represented by formula (II), in a process for preparing a compound represented by formula (I):

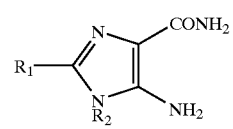

(I)

wherein $R_1$ and $R_2$ are the same as defined above, and wherein a process for preparing the compound represented by the formula (II) comprises one of the following:

a) a compound represented by formula (III)

(III)

wherein $R_1$ represents the same as defined above and $R_3$ represents an alkyl group of C1 to C6, is reacted with ammonia in C1 to C5 alcohol, wherein $R_1$ represents the same as defined above and $R_2$ represents a hydrogen atom;

b) a compound of the formula (V): $R_1CN$ wherein $R_1$ represents an alkyl group of C1 to C10 which may have substituents a hydrocarbon group of C3 to C14 having alicyclic skeletons, an alkenyl group which may have substituents, an alkynyl group which may have substituents, an aryl 2group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group, is reacted with diaminomaleonitrile in the presence of an acid; and c) diaminomaleonitrile and a compound represented by formula (VI): $R_1CONHR_2$ wherein $R_1$ and $R_2$ each independently represent a hydrogen atom, an alkyl group of C1 to C10 which may have substituents, a hydrocarbon group of C3 to C14 having alicyclic skeletons, an alkenyl group which may have substituents an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group, are reacted with a compound selected from the group consisting of phosphorous oxychloride, phosphorous trichloride, phosphorous pentachloride, phosphorous oxybromide, diphosphoryl chloride, sulfonyl chloride, sulfuryl chloride, phosgene, diphosgene, triphosgene, and chloroformate trichloromethyl ester.

2. A process for the preparation characterized in that a compound represented by formula (II):

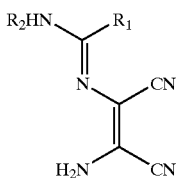

wherein $R_1$ represents a hydrogen atom an alkyl group of $C_1$ to $C_{10}$ which may have substituents, a hydrocarbon group of $C_3$ to $C_{14}$ having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group; and $R_2$ represents a hydrogen atom and/or in inorganic salt thereof are cyclized and hydrolyzed in an aqueous basic solution involving 1–10 moles of a basic compound per 1 mole of the compound represented by formula (II), followed by adjusting the pH to the isoelectric point to precipitate crystal in a process for preparing a compound represented by formula (I):

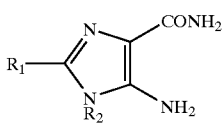

wherein $R_1$ and $R_2$ represent the same as defined above, and
wherein a process for preparing the compound represented by the formula (II) comprises one of the following:
a) a compound represented by formula (III)

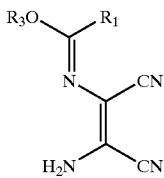

wherein $R_1$ represents the same as defined above and $R_3$ represents an alkyl group of C1 to C6, is reacted with ammonia in C1 to C5 alcohol, wherein $R_1$ represents the same as defined above and $R_2$ represents a hydrogen atom:
b) a compound of the formula (V): $R_1CN$ wherein $R_1$ represents an alkyl group of C1 to C10 which may have substituents, a hydrocarbon group of C3 to C14 having alicyclic skeletons, an alkenyl group which may have substituents, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group, is reacted with diaminomaleonitrile in the presence of an acid; and
c) diaminomaleonitrile and a compound represented by formula (VI): $R_1CONHR_2$ wherein $R_1$ and $R_2$ each independently represent a hydrogen atom, an alkyl group of C1 to C10 which may have substituents, a hydrocarbon group of C3 to C14 having alicyclic skeleton, an alkenyl group which may have substituents, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group, are reacted with a compound selected from the group consisting of phosphorous oxychloride, phosphorous trichloride phosphorous pentachloride, phosphorous oxybromide, diphosphoryl chloride, sulfonyl chloride, sulfuryl chloride, phosgene, diphosgene, triphosgene, and chloroformate trichloromethyl ester.

3. A process for the preparation characterized in that a compound represented by formula (II):

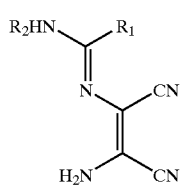

wherein $R_1$ represents a hydrogen atom, an alkyl group of $C_1$ to $C_{10}$ which may have substituents, a hydrocarbon group of $C_3$ to $C_{14}$ having alicyclic skeletons, an alkynyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group; and $R_2$ represents a hydrogen atom and/or an inorganic salt thereof are cyclized and hydrolyzed in an aqueous basic solution involving 1–10 moles of a basic compound per 1 mole of the compound represented by formula (II), followed by adjusting the pH to 9 to 13 to precipitate crystal in a process for preparing a compound represented by formula (I):

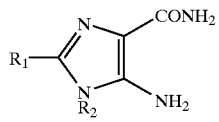

wherein $R_1$ and $R_2$ represent the same as defined above, and
wherein a process for preparing the compound represented by the formula (II) comprises one of the following:
a) a compound represented by formula (III)

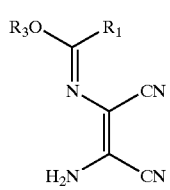

wherein $R_1$ represents the same as defined above and $R_3$ represents an alkyl group of C1 to C6, is reacted with ammonia in C1 to C5 alcohol, wherein $R_1$ represents the same as defined above and $R_2$ represents a hydrogen atom;

b) a compound of the formula (V): $R_1CN$ wherein $R_1$ represents an alkyl group of C1 to C10 which may have substituents, a hydrocarbon group of C3 to C14 having alicyclic skeletons, an alkenyl group which may have substituents, an aralkyl group which may have substituents, an aryl group which may have substituents, an aralkyl group which may have substituents, a heterocyclic group which may have substituents, a heterocyclic alkyl group which may have substituents, an N-unsubstituted or substituted carbamoyl group, or an alkoxycarbonyl group, is reacted with diaminomaleonitrile in the presence of an acid; and c) diaminomaleonitrile and a compound represented by formula (VI): $R_1CONHR_2$ wherein $R_1$ and $R_2$ each independently represent a hydrogen atom, an alkyl group of C1 to C10 which may have substituents, a hydrocarbon group of C3 to C14 having alicyclic skeletons, an alkenyl group which may have substituents, an alkynyl group which may have substituents, an aryl group which may have substituents, an aralkyl group which may have substituents, a heterocyclic group which may have substituents, a heterocyclic alkyl group which way have substituents, an N-unsubstituted or substituted carbamoyl group, or an alkoxycarbonyl group, are reacted with a compound selected from the group consisting of phosphorous oxychloride, phosphorous trichloride, phosphorous pentachloride, phosphorous oxybromide, diphosphoryl chloride, sulfonyl chloride, sulfuryl chloride, phosgene, diphosgene, triphosgene, and chloroformate trichloromethyl ester.

4. The process for the preparation according to claim 3 characterized in that the pH is adjusted to a range of 11 to 12.

5. The process for the preparation as in any one of claims 1, 2, 3 and 4 characterized in that the basic compound is sodium hydroxide or potassium hydroxide.

6. The process for the preparation as in any one of claims 1, 2, and 3, wherein $R_1$ in formulae (I) through (II) is a hydrogen atom, an unsubstituted alkyl group of $C_1$ to $C_{10}$ having straight or branched chains, an alkyl group having straight or branched chains substituted with halogen atoms, hydroxyl, alkoxy, acyloxy, carbamoyl, oxy, hydroxyalkyl, alkoxyalkyl, hydroxycarbonyl, alkoxycarbonyl, amino groups, a hydrocarbon group of $C_3$ to $C_{14}$ having alicyclic skeletons, an unsubstituted alkenyl group of $C_1$ to C10 having straight or branched chains, an alkenyl group having straight or branched chains substituted with halogen atoms, hydroxyl, alkoxy, phenyl, substituted phenyl groups, an unsubstituted alkynyl group of $C_1$ to $C_{10}$ having straight ox branched chains, an alkynyl group having straight or branched chains substituted with halogen atoms, hydroxyl, alkoxy, phenyl, substituted phenyl groups, a phenyl group, a phenyl group substituted with halogen atoms, alkyl, alkoxy, phenyl, substituted phenyl, heterocyclic, aralkyl, heterocyclic alkyl groups, an unsubstituted aralkyl group having straight or branched chains, an aralkyl group having straight or branched chains substituted with halogen atoms, alkyl, alkoxy, phenyl, substituted phenyl, heterocyclic, aralkyl, heterocyclic alkyl groups, an unsubstituted heterocyclic group, a heterocyclic group substituted with halogen atoms, alkyl alkoxy, phenyl, substituted phenyl, heterocyclic, aralkyl, heterocyclic alkyl groups, an unsubstituted heterocyclic alkyl group having straight or branched chains, a heterocyclic alkyl group having straight or branched chains substituted with halogen atoms, alkyl, alkoxy, phenyl, substituted phenyl, heterocyclic, aralkyl, heterocyclic alkyl groups, an N-unsubstituted or substituted carbamoyl group, or an alkoxycarbonyl group.

7. The process for the preparation according to claim 1 wherein $R_2$ in formulae (I) and (II) is an unsubstituted alkyl group of $C_1$ to $C_{10}$ having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups, a hydrocabon group of $C_3$ to $C_{14}$ having alicyclic skeletons, an unsubstituted alkenyl group of $C_1$ to C10 having straight or branched chains, an alkenyl group of $C_1$ to $C_{10}$ having straight or branched chains substituted with halogen atoms, hydroxyl, alkoxy, phenyl, substituted phenyl groups, an unsubstituted alkynyl group of $C_1$ to $C_{10}$ having straight or branched chains, an alkynyl group having straight or branched chains substituted with halogen atoms, hydroxyl, alkoxy, phenyl, substituted phenyl groups, a phenyl group a phenyl group substituted with halogen atoms, alkyl, alkoxy, phenyl, substituted phenyl, heterocyclic, aralkyl, heterocyclic alkyl groups, an unsubstituted arylkyl group having straight or branched chains, an aralkyl group having straight or branched chains substituted with halogen atoms, alkyl, alkoxy, phenyl, substituted phenyl, heterocyclic, aralkyl, heterocyclic alkyl groups, an unsubstituted heterocyclic group, a heterocyclic group substituted with halogen atoms, alkyl, alkoxy, phenyl, substituted phenyl, heterocyclic, aralkyl, heterocyclic alkyl groups, an unsubstituted heterocyclic alkyl group having straight or branched chains, a heterocyclic alkyl group having straight or branched chains substituted with halogen atoms, alkyl, alkoxy, phenyl, substituted phenyl, heterocyclic, aralkyl, heterocyclic alkyl groups, an N-unsubstituted or substituted carbamoyl group, or an alkoxycarbonyl group.

8. The process for preparation as any one of claims 1, 2, and 3 wherein $R_1$ in formulae (I) through (II) is a hydrogen atom, an unsubstituted alkyl group of $C_1$ to $C_{10}$ having straight or branched chains, an alkyl group having straight or branched chains substituted with halogen atoms, hydroxyl, alkoxy, acyloxy, carbamoyloxy, hydroxyalkyl, alkoxyalkyl, hydroxycarbonyl, alkoxycarbonyl, amino groups.

9. The process for the preparation as in any one of claims 1, 2, and 3 wherein $R_1$ in general formulae (I) through (II) is an unsubstituted alkyl group of $C_1$ to $C_{10}$ having straight or branched chains.

* * * * *

UNITED STATES PATENT AND TRADEMARK OFFICE
CERTIFICATE OF CORRECTION

PATENT NO.     : 6,797,828 B1
DATED          : September 28, 2004
INVENTOR(S)    : Hiroaki Shibasaki et al.

It is certified that error appears in the above-identified patent and that said Letters Patent is hereby corrected as shown below:

Column 2,
Line 41, replace "amino-1-, 2-@3diaminovinyl)" with -- amino-l-, 1-diaminovinyl --.

Column 9,
Line 48, replace "4-acetoxyl3-" with -- 4-acetoxy-3- --.
Line 49, replace "acetoxymethyl1-butyl," with -- acetoxymethyl-butyl, --.
Line 49, replace "4-hydroxyl3-hydroxymethyl1-butyl," with -- 4-hydroxy-3-hydroxymethyl-butyl, --.
Line 50, replace "2-hydroxyl1-hydroxymethyl1-" with -- 2-hydroxy-l-hydroxymethyl- --.
Line 51, replace "4-hydroxy12-hydroxymethyl1-butyl," with -- 4-hydroxy-2-hydroxymethyl-butyl, --.
Line 58, replace "[2,2,1] hepta-2, 3-epoxyl5-yl," with -- [2,2,1] hepta-2, 3-epoxy-5-yl, --.
Line 64, replace "3-hydroxyl1-butenyl," with -- 3-hydroxy-1-butenyl, --.
Line 65, replace "3-methoxyl2-propenyl" with -- 3-methoxy-2-propenyl --.

Column 10,
Line 1, replace "3-hydroxyl1-butenyl, 3-alkoxyl1-" with -- 3-hydroxy-l-butenyl, 3-alkoxy-1- --.
Line 9, replace "groups andthe like." with -- groups and the like. --.
Line 15, replace "3-9" with -- 3- --.
Line 17, replace "4-phenyl-1-methylmethyl" with -- 4-phenyl-phenyl-l-methylmethyl --.
Line 20, replace "6-methoxyl2-pyridyl," with -- 6-methoxy-2-pyridyl, --.
Line 24, replace "5-benzylamino-5-deoxylβ-D-ribofuranosyl," with -- 5-benzylamino-5-deoxy-β-D-ribofuranosyl, --.
Line 24, replace "5-O-methy1β-" with -- 5-O-methyl-β --.
Line 25, replace "5-phosphonyl-5-deoxyB-D-ribofuranosyl," with -- 5-phosphonyl-5-deoxy-B-D-ribofuranosyl, --.
Line 26, replace "2-deoxyl-β-D-arabinofuranosyl," with -- 2-deoxy-β-D-arabinofuranosyl, --.
Line 26, replace "2-deoxylβ-D-ribofuranosyl" with -- 2-deoxy-β-D-ribofuranosyl --.
Line 30, replace "6-metboxyl2-pyridylmethyl," with -- 6-methoxy-2-pyridylmethyl, --.
Line 33, replace "1-methyl1-5-chloro-4-pyrazolylmethyl" with -- 1-methyl-5-chloro-4-pyrazolylmethyl--.

Column 11,
Line 39, replace "n-penyl" with -- n-pentyl --.
Line 58, replace "n-propatol" with -- n-propanol --.
Line 67, replace "preferably 0 to 100°C. is" with -- preferably 0 to 10°C. is --.

UNITED STATES PATENT AND TRADEMARK OFFICE
CERTIFICATE OF CORRECTION

PATENT NO. : 6,797,828 B1
DATED : September 28, 2004
INVENTOR(S) : Hiroaki Shibasaki et al.

It is certified that error appears in the above-identified patent and that said Letters Patent is hereby corrected as shown below:

Column 13,
Line 11, replace "nitrites" with -- nitriles --.

Column 14,
Line 4, replace "sulfurylchloride" with -- sulfuryl chloride --.

Column 15,
Line 26, replace "50°C." with --5°C.--
Line 31, replace "N-(2-amino 1,2-9 dicyanovinyl)" with -- N-(2-amino 1,2-dicyanovinyl) --.
Line 32, replace "1H NMR" with -- 1HNMR --.
Line 44, remove "1H"
Line 45, replace "NMR" with -- 1HNMR --.
Line 59, replace "1H NMR" with -- 1HNMR --.

Column 16,
Line 5, remove "1H"
Line 6, replace "NMR" with -- 1HNMR --.
Line 20, replace "purity: 95.1" with -- purity: 95.1% --.

Column 18,
Line 35, replace "substituents a hydrocarbon group" with -- substituents, a hydrocarbon group --.
Line 38, replace "an aryl 2group" with -- an aryl group --.
Line 53, replace "ents an alkenyl group" with -- ents, an alkenyl group --.

Column 19,
Line 1, replace "hydrogen atom an alkyl group" with -- hydrogen atom, an alkyl group --.

Column 20,
Line 3, replace "skeleton," with -- skeletons, --.

Column 21,
Line 5, replace "an aralkyl group" with -- an alkynyl group --.
Line 53, replace "ox" with -- or --.

UNITED STATES PATENT AND TRADEMARK OFFICE
CERTIFICATE OF CORRECTION

PATENT NO. : 6,797,828 B1
DATED : September 28, 2004
INVENTOR(S) : Hiroaki Shibasaki et al.

It is certified that error appears in the above-identified patent and that said Letters Patent is hereby corrected as shown below:

Column 22,
Line 1, replace "alkyl" with -- alkyl, --.
Line 20, replace "hydrocabon" with -- hydrocarbon --.
Line 53, replace "as any one" with -- as in any one --.

Signed and Sealed this

First Day of February, 2005

JON W. DUDAS
*Director of the United States Patent and Trademark Office*